Figure 1:
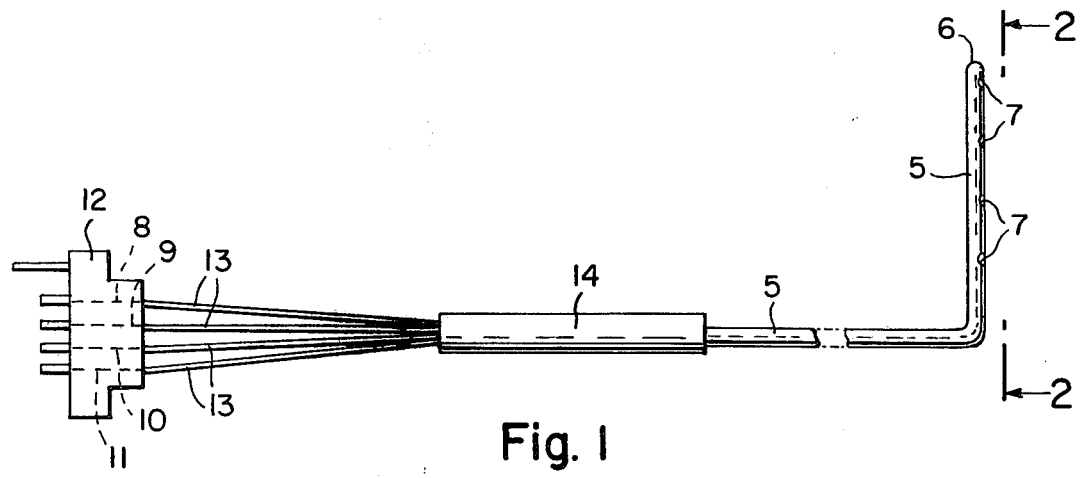

United States Patent [19]

Kline

[11] 4,172,451

[45] Oct. 30, 1979

[54] INTRACARDIAL ELECTRODE AND A METHOD OF MANUFACTURE THEREOF

[75] Inventor: William M. Kline, Gloversville, N.Y.

[73] Assignee: Medical Evaluation Devices and Instruments Corp., Gloversville, N.Y.

[21] Appl. No.: 893,964

[22] Filed: Apr. 6, 1978

[51] Int. Cl.² ............................................. A61B 5/04
[52] U.S. Cl. .................................................. 128/642
[58] Field of Search ......... 128/2.06 F, 2.1 E, DIG. 4, 128/404, 418, 419 P

[56] References Cited
U.S. PATENT DOCUMENTS

| 3,216,424 | 11/1965 | Chardack | 128/418 |
| 3,516,412 | 6/1970 | Ackerman | 128/418 |
| 3,804,098 | 4/1974 | Friedman | 128/404 |
| 3,995,623 | 12/1976 | Blake et al. | 128/404 |

OTHER PUBLICATIONS

O'Riordan et al., "American Journal of Cardiology" vol. 39, #4, Apr. 1977, pp. 529-536.
Pollak, "Medical and Biological Engineering" v. 9, #6, pp. 657-664 (only p. 658 of interest) Nov. 1971.
Johnston et al., "IBM Technical Disclosure Bulletin" vol. 6, #8, Jan. 1964, pp. 13-14.

Primary Examiner—William E. Kamm
Attorney, Agent, or Firm—Thomas E. Tate

[57] ABSTRACT

An indwelling multi-contact plunge electrode to measure the electrical output from areas of the myocardium on an individual, sequential or combination composite basis. The electrode comprises an outer flexible tube containing a plurality of wire leads having their distal ends projecting angularly through the wall of the tube adjacent the distal end thereof and their proximal ends connected to an electrical plug. The distal end portion of the electrode is stiffened and bent at a substantial angle to the proximal portion and the void in the lumen of the tube not occupied by the wire leads is filled with silicone rubber.

9 Claims, 2 Drawing Figures

INTRACARDIAL ELECTRODE AND A METHOD OF MANUFACTURE THEREOF

THE INVENTION

This invention relates generally to new and useful improvements in intracardial electrodes and particularly seeks to provide an indwelling multicontact plunge electrode that can be used to measure electrical outputs at mutiple depths within the myocardial wall of the heart of an animate being on an individual, sequential or combination basis.

Such electrodes must be capable of receiving and transmitting electrical impulses from strata of the heart to a recording and/or information storage unit for either direct observation or subsequent analysis; and should be capable of providing selected single location signals to the recording unit or providing sequential signals or providing selected group signals thereto as determined by the control settings of the recording unit.

These multiple readings are in direct contrast to the single readings heretofore obtainable with known types of single contact plunge probes or electrodes and are opposite in sense in comparison with the imposed timed electrical stimuli provided by single or plural contact catheters such as those employed in atrial pacing of a heart. Typical examples of the latter types of pacing catheters are listed on pages 2–9 of the 1975 catalog of the United States Catheter and Instruments Corp. (U.S.-C.I.).

It is apparent that scientific investigation of coronary arterial stenoses can be greatly aided through the use of electrograms that can only be made in connection with multicontact plunge electrodes. In this context, attention is drawn to the April 1977 issue of The American Journal of Cardiology, Volume 39, pages 529–536, in which a study of John B. O'Riordan, MB, and coauthors, is reported. Although that article describes the general nature of a multicontact electrode experimentally developed by this inventor, it does not describe either the exact construction being tested at that time, nor does it constitute a prior printed publication with respect to the electrode specifically disclosed and claimed herein.

Therefore, an object of this invention is to provide a multicontact intramyocardial electrode that is particularly adaptable for use in connection with recording instruments employed in the scientific investigations and observations of coronary arterial stenoses and other conditions where multiple depths readouts are required from a single electrode.

Another object of this invention is to provide an electrode of the character stated that includes an outer tube or sheath of a fluorinated hydrocarbon that is smooth, inert, flexible, thrombo-resistant, non-thrombogenic and which may be either radiopaque or non-radiopaque.

Another object of this invention is to provide an electrode of the character stated in which the outer tube or sheath is provided at its distal tip with a smooth generally hemispherical closure and contains within its lumen from two to twelve insulated lead wires, the distal ends of which project angularly through the tube wall at regularly spaced intervals along the distal end portion of the tube and have their exposed ends substantially coplanar with the outer surface of the tube, the proximal ends of which project proximally beyond the proximal end of the tube for connection to an electrical plug.

Another object of this invention is to provide an electrode of the character stated in which that portion of the tube lumen not occupied by the insulated lead wires preferably is filled with a material such as a silicone room temperature vulcanizing rubber to prevent relative movement between the lead wires and to render the entire tube structure laterally compression resistant while retaining its flexibility.

A further object of this invention is to provide an electrode of the character stated in which the distal end portion containing the exposed ends of the lead wires is bent substantially at a right angle to the proximal portion and is stiffened by an axially disposed pin having a short leg extending into the proximal portion.

A further object of this invention is to provide a novel method of forming an electrode of the character stated.

A further object of this invention is to provide an electrode of the character stated that is intended to be disposable after a single use.

A further object of this invention is to provide an electrode of the character stated that is simple in design, rugged in construction and economical to manufacture.

With these and other objects, the nature of which will become apparent, the invention will be more fully understood by reference to the drawings, the accompanying detailed description and the appended claims.

Figure 2:
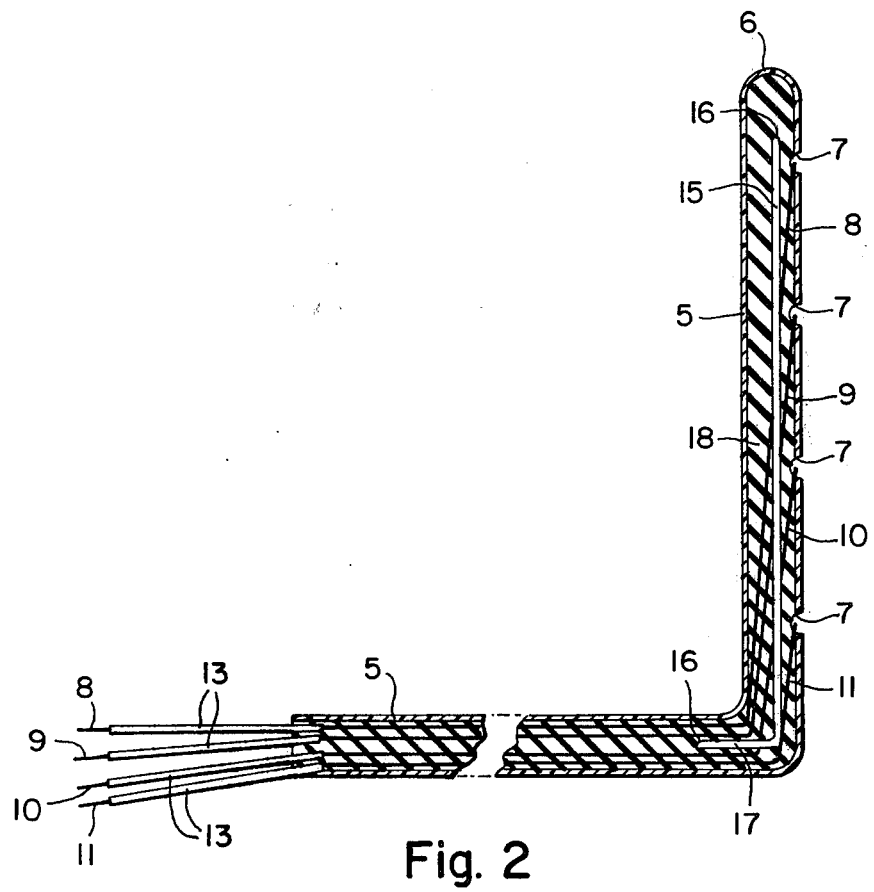

In the drawings:

FIG. 1 is a side elevation of a complete 4-lead electrode constructed in accordance with this invention; and FIG. 2 is an enlarged longitudinal section of the distal end portion of the electrode taken along the line 2—2 of FIG. 1.

Referring to the drawings in detail, a 4-lead electrode, as one example, includes an outer tube or sheath 5, preferably formed from a fluorinated hydrocarbon such as a FEP (hexafluoropropylene-tetrafluoroethylene copolymer) or TFE (tetrafluorocthylene) resin, commercially available as "Teflon" FEP or "Teflon" TFE from DuPont, which may be from about 50 to 150 cm. in length or more and, for a No. 3 French size, should have an O.D. (outside diameter) of 0.038" and an I.D. (inside diameter) of 0.026".

These electrodes can be fabricated within the size range of No. 2 French to about No. 6 French, in which the O.D.s would range from 0.025" to 0.075" and the I.D.s preferably would range from 0.016" to 0.065".

The distal tip of the tube 5 is formed into a smooth generally hemispherical closure 6 and the prominal end of the tube is open.

The distal end portion of the tube 5, for a four lead electrode, is provided with four longitudinally aligned angularly oriented perforations 7, the axes of which are disposed at about a 30° angle with respect to the longitudinal axis of the tube. Preferably, the distalmost perforation 7 should be located approximately 0.030" from the closure 6 and the spacing between the perforations should be on the order of 5 mm.

Four wire leads 8, 9, 10 and 11 are contained within the lumen of the tube 5 and have their distal ends extending through the perforations 7 and their proximal ends projecting about 10 cm. proximally beyond the proximal end of the tube for connection to an electrical plug 12. The distal ends of the leads 8–11 are ground and polished into generally coplanar relationship to the outer surface of the tube 5 to provide exposed contacts. The exposed proximal ends of the leads 8–11 are individually protected by "spaghetti" tubes 13 and an outer sleeve 14 protects the proximal end portion of the unit. Preferably the "spaghetti" tubes 13 and the sleeve 14 are formed from the same type of material as used to form the tube 5, although any other suitable type of inert plastic material such as polyethylene, polypropylene or polyurethane could be used instead.

Each of the leads 8–11 preferably is formed from 300 Series stainless steel ribbon wire having a cross-section of 0.003"×0.010", although the range of usable cross-sectional sizes may extend from about 0.0015"×0.004" to about 0.010"×0.025". Precious metals such as silver, gold or platinum could also be used for the leads.

It is important that the leads 8–11 be coated by a smooth, low-friction, flexible, continuous, insulating coating such as that provided by a FEP or TFE resin; and a preferred method of applying such a coating to the leads is disclosed in U. S. Pat. No. 3,922,378, granted Nov. 25, 1975, in which a wire substrate is immersed in a dispersion bath of the selected resin and removed therefrom, then the coated substrate is initially dried, then heated to a predetermined temperature over a predetermined period of time and finally slowly cooled over a predetermined period of time to a temperature as low as or lower than a predetermined lower temperature.

The distal end portion of the tube 5 is provided with an axially disposed stainless steel wire stiffening pin 15 that extends from a location adjacent the distal closure 6 to a location proximal of the proximalmost of the perforations 7 and includes rounded ends 16, 16 in order to avoid either scraping of the insulating coating on the leads 8–11 or perforating the end closure 6.

The distal end portion of the electrode that includes the perforation 7, the distal ends of the leads 8–11 and the major portion of the pin 15, is bent at about 90° to the proximal portion of the electrode to define a plunge portion that can be directly introduced into the myocardium of a heart and to leave a proximally extending short leg 17 of the pin 15 against which the insertion force is exerted.

That portion of the void in the lumen of the tube 5 that is not occupied by the leads 8–11 and the stiffening pin 15 is filled by a cured flexible insulating material 18 such as a silicone RTV (room temperature vulcanizing) rubber, which protects the leads 8–11 from potential damage due to relative movements due to torsion or flexing and renders the complete assembly of the electrode substantially resistant to lateral compression.

Because the method of assembly of this electrode is quite important to the utility and functional integrity of the finished product, a brief description thereof now will be presented.

First, the tubing 5 is cut to length (50–150 cm. or more) and then the distal end portion is pierced to provide the angularly disposed, longitudinally aligned, perforations 7. Then the coated wire leads 8–11 are inserted from the outside of the tube 5 through the performations 7 into and proximally through the lumen of the tube, leaving distal ends of the leads projecting externally of the wall of the tube and the proximal ends of the leads projecting substantially beyond the proximal end of the tube. This insertion of the leads 8–11 is readily effected because the wires are relatively stiff and because frictional resistance to their passage is at a minimum due to the low friction characteristics of both the wire coatings and the tube 5.

Next a solution of the RTV silicone rubber is prepared and vacuum-introduced into the void of the lumen of the tube 5 that is not occupied by the leads 8–11. This requires a vacuum on the order of 28" hg. in order to assure a complete flow-through of the RTV solution.

Preferably, the silicone rubber solution comprises 80 parts of a RTV base, as commercially available from the General Electric Company, and 20 parts of G.E.'s 910 diluent, although the range of base to diluent may extend from about 95 parts base and 5 parts diluent to 60 parts base and 40 parts diluent.

Next, the pin 15 is axially inserted from the open distal end of the tube 5 into the filled lumen thereof to a distance such that the distal end of the pin is located slightly distally beyond the distal one of the perforations 7.

Next, the RTV filled tube is cured either by storage overnight at room temperature or by heating at about 150° C. for about 30 minutes. Then the outer surface of the tube 5 is wiped clean and a small amount of the cured RTV is removed from the open distal end of the tube 5 to enable the distal tip thereof to be shaped by heat, mechanical deformation and grinding and polishing into the generally hemispherical closure 6.

Next, the proximal ends of the leads 8–11 are connected to the plug 12 after adding the "spaghetti" 13 and the protective sleeve 14; and then electrical continuity of the leads from the perforations 7 to the plug 12 is checked and each contact pin of the plug is appropriately marked with the identity of its associated lead.

Next, the distal end portion of the electrode is cleaned and then bent at a substantial right angle to the proximal portion, leaving the leg 17 of the pin 15 extending into the proximal portion.

Finally, the outwardly projecting distal ends of the leads 8–11 are clipped off close to the outer surface of the tube 5 and are finely ground and polished into substantially coplanar relationship therewith. It should be noted that since the leads 8–12 are oriented at an acute angle relative to the longitudinal axis of the tube 5, the exposed ground and polished contact areas thereof are larger than their 90° cross-sectional areas.

It is of course to be understood that variations in arrangements, materials of construction and proportions of parts may be made within the scope of the appended claims.

I claim:

1. In an indwelling intramyocardial electrode, a lumen-defining flexible tubular body having proximal and distal ends and formed from an inert, thrombo-resistant, non-thrombogenic plastic material, a generally hemispherical closure closing the distal end of said tubular body; a plurality of insulated wire leads contained within the lumen of said tubular body and having proximal and distal ends, the distal ends of said wire leads being angularly retained by the wall of said tubular body in a spaced longitudinal row along the distal end portion thereof, the distal end of each said wire lead being substantially coplanar with the outer surface of said tubular body to define an exposed contact area, the proximal ends of said wire leads extending proximally beyond the proximal end of said tubular body, each of said wire leads being formed from ribbon wire of generally rectangular cross-section; means contained within the lumen of said tubular body for stiffening the distal end portion thereof that at least includes the exposed distal ends of said wire leads, said means comprising an axially disposed pin extending from a location adjacent said generally hemi-spherical closure to a location proximal of the proximal-most of said wire leads, the stiffened distal end portion of said tubular body being permanently bent at a substantial angle with respect to the proximal portion thereof; and a flexible filler material filling that portion of the lumen of said tubular body that is not occupied by said wire leads and by said stiffening pin.

2. The electrode of claim 1 in which said filler material is silicone rubber.

3. The electrode of claim 1 in which the material for said ribbon wire is stainless steel.

4. The electrode of claim 1 in which the material for said ribbon wire is silver.

5. The electrode of claim 1 in which the material for said ribbon wire is gold.

6. The electrode of claim 1 in which the material for said ribbon wire is platinum.

7. In a method of forming an electrode for transmitting intramyocardial output the steps of; cutting a lumen-defining flexible tubular body having proximal and distal ends to a predetermined length; piercing the distal end portion of the wall of said tubular body with a plurality of longitudinally aligned angularly oriented perforations for the reception and retention of the distal ends of an equal number of wire leads; passing a plurality of insulated wire leads through said perforations into and along the lumen of said tubular body, the distal ends of said wire leads initially extending exteriorly of said tubular body and the proximal ends of said wire leads extending proximally beyond the proximal end of said tubular body; filling that portion of the lumen of said tubular body not occupied by said wire leads with a flexible filler material; axially inserting a stiffening pin into the distal end portion of said tubular body and removing any of said filler material displaced as the result of inserting said stiffening pin; sealing the distal end of said tubular body by a generally hemi-spherical closure; severing the projecting distal ends of said wire leads close to the outer surface of said tubular body and fine grinding and polishing the remaining exposed end portions thereof into substantial coplanar relation with the outer surface of said tubular body whereby to define exteriorally exposed contacts.

8. The method of claim 7 additionally including the steps of connecting each of said wire leads to an associated contact pin in an electrical plug, checking the electrical continuity of each of said wire leads to the proximal end thereof at its said associated contact pin and marking each said contact pin with the identity of its associated wire lead.

9. The method of claim 7 additionally including the step of bending the assembled stiffened distal end portion of said electrode at a substantial angle to the proximal portion thereof whereby to enable the thus bent distal end portion to serve as a plunge for insertion into the myocardium of a heart.

* * * * *